United States Patent [19]

Terry, Jr. et al.

[11] Patent Number: 5,335,657

[45] Date of Patent: Aug. 9, 1994

[54] THERAPEUTIC TREATMENT OF SLEEP DISORDER BY NERVE STIMULATION

[75] Inventors: Reese S. Terry, Jr., Houston; Joachim F. Wernicke, League City, both of Tex.

[73] Assignee: Cyberonics, Inc., Webster, Tex.

[21] Appl. No.: 695,558

[22] Filed: May 3, 1991

[51] Int. Cl.⁵ ............................................. A61N 1/36
[52] U.S. Cl. .................................................. 607/45
[58] Field of Search ........... 128/419 S, 419 G, 419 R, 128/421, 422, 423 R; 600/28; 607/42, 44, 45, 72

[56] References Cited

U.S. PATENT DOCUMENTS 4,715,367 12/1987 Crossley ........................... 128/419 R
4,830,008  5/1989 Meer .................................. 128/421
5,025,807  6/1991 Zabara ............................... 128/421

Primary Examiner—William E. Kamm
Attorney, Agent, or Firm—O'Connor, Cavanagh et al.

[57] ABSTRACT

Method and apparatus for treating and controlling sleep disorders by detecting the presence of the sleep disorder under treatment, and, in response, selectively applying a predetermined electrical signal to the patient's vagus nerve for stimulation thereof to alleviate the sleep disorder under treatment. The method and apparatus includes several techniques for detecting the presence of the sleep disorder under treatment, such as sensing the patient's EEG activity in the case of insomniac and hypersomniac patients, or detecting a sudden nodding of the head in the case of narcoleptic patients, or sensing the cessation of respiration in the case of sleep apnea patients.

36 Claims, 5 Drawing Sheets

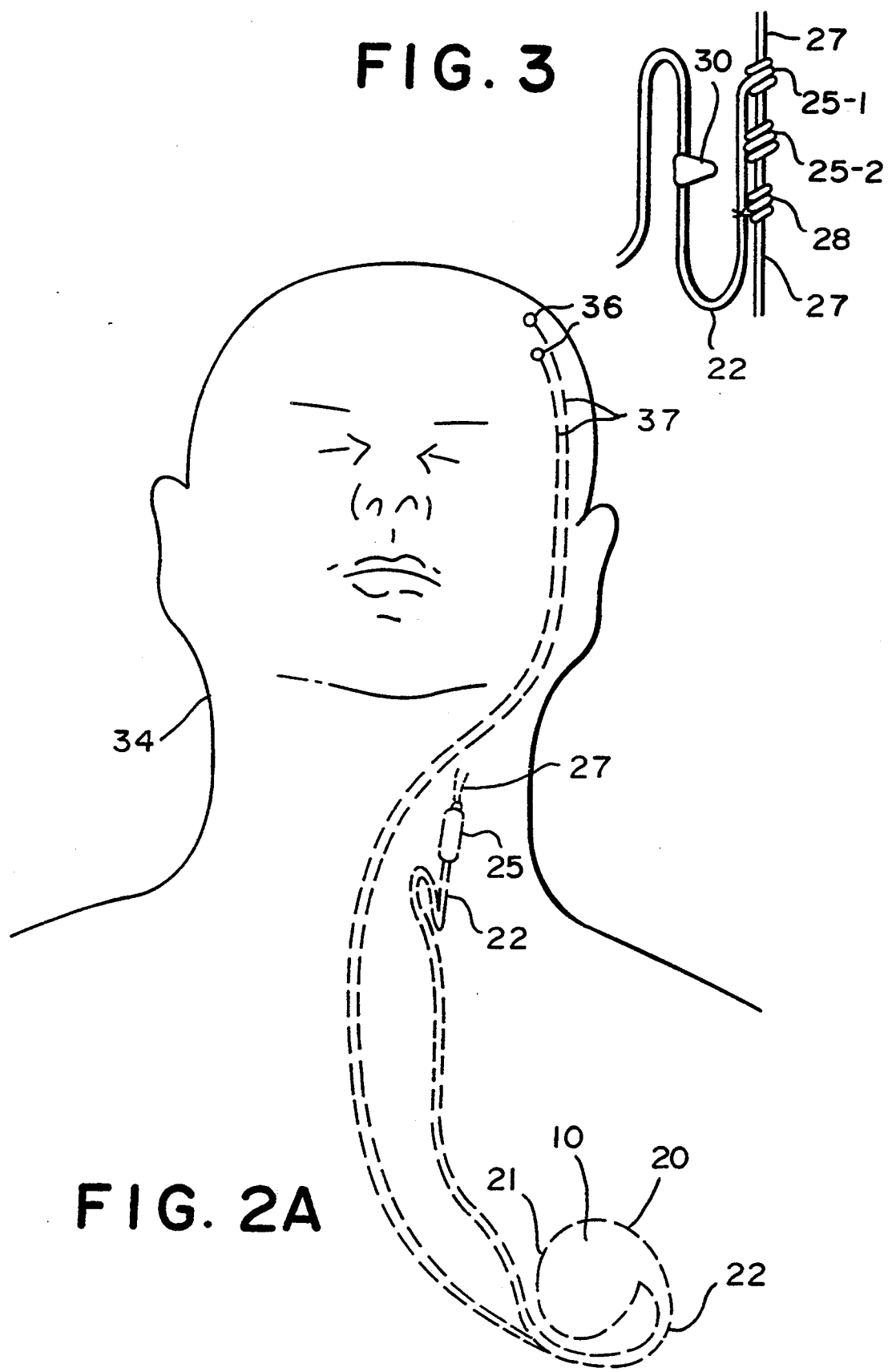

THERAPEUTIC TREATMENT OF SLEEP DISORDER BY NERVE STIMULATION

BACKGROUND OF THE INVENTION

The present invention relates generally to methods and apparatus for treating or controlling medical, psychiatric or neurological disorders by application of modulating electrical signals to a selected nerve or nerve bundle of the patient, and more particularly to techniques for treating patients with sleep disorders by application of such signals to a cranial nerve, using an implantable neurostimulating device. Specifically, the invention is directed toward treating various sleep disorders, such as insomnia, hypersomnia, apnea, and narcolepsy, by selective modulation of vagus nerve electrical activity.

Sleep is not a uniform state, but rather involves several stages characterized by changes in the individual's EEG. Stage 1 sleep is drowsiness, in which the EEG displays a lower voltage, more mixed frequencies and deterioration of alpha rhythm relative to the EEG when the individual is awake, even when in a relaxed state. In stage 2, background activity similar to that of stage 1 is experienced, with bursts of slightly higher frequency "sleep spindles" and sporadic higher amplitude slow wave complexes. The third and fourth stages of sleep display increasing high amplitude slow wave activity. A separate sleep stage is one in which the individual undergoes rapid eye movements (REM) with lower voltage, higher frequency EEG and other characteristics similar to those which occur when the individual is awake, whereas the other four sleep stages are categorized as non-REM (NREM) sleep.

Normally, the extent to which NREM stages and REM sleep are experienced, as well as the sleep requirements of the individual, are largely age dependent. Adults typically pass in sequence through the four stages of NREM sleep, and may enter several spaced periods of REM sleep during the night. Adults usually require only six or seven hours of sleep, while infants require sleep during both day and night (normally 50% of the sleep time being spent in REM sleep), and the aged require less sleep than the adult and may experience no REM sleep.

The principal sleep disorders are central sleep apnea, insomnia and hypersomnia, and the syndromes thereof. Other sleep disorders include sleep walking and enuresis (nocturnal incontinence, or bed-wetting). The latter two disorders are primarily confined to children. Insomnia is a chronic inability to sleep or to remain asleep throughout the night, and is usually suffered as a result of various physical and/or physiologic factors, such as pain, discomfort, anxiety, depression, tension, and obstructive sleep apneas. Sleep apneas are characterized by brief episodes of respiratory arrest, which may occur many times during sleep and may be associated with obstruction of the upper airways, cessation of diaphragmatic movements and snoring. Hypersomnia is a condition in which the individual undergoes sleep of excessive depth or abnormal duration, usually caused by physiologic rather than physical factors and characterized by a state of confusion on awakening. Daytime hypersomnia, which may complicate sleep apnea, is commonly represented by the narcoleptic syndrome, characterized by sudden sleep attacks, cataplexy, sleep paralysis, and visual or auditory hallucinations at the onset of sleep.

Conventional treatment of insomnia typically involves hypnotics (drugs employed as sedatives), while treatment of narcolepsy and other syndromes of hypersomnia often utilizes stimulant drugs such as dextro- and laevo-amphetamine and methylphenidate. Unfortunately, however, treatment with drugs has not proved very effective and often results in undesirable side-effects.

It is a principal object of the present invention to apply techniques of selective modulation of the electrical activity of a cranial nerve, and particularly the vagus nerve, to treat and control at least the principal sleep disorders, including sleep apnea, insomnia, hypersomnia, narcolepsy, and syndromes thereof.

In addressing a therapy involving nerve stimulation to treat sleep disorders, notice should be taken of existing knowledge that most nerves in the human body are composed of thousands of fibers, having different sizes designated by groups A, B and C, carrying signals to and from the brain and other parts of the body. The vagus nerve, for example, may have approximately 100,000 fibers (axons) of the three different types, each of which carries such signals. Each axon of that nerve only conducts in one direction, in normal circumstances. The A and B fibers are myelinated, that is, they have a myelin sheath in the form of a substance largely composed of fat. On the other hand, the C fibers are unmyelinated.

Myelinated fibers are typically larger, have faster electrical conduction and much lower electrical stimulation thresholds than the unmyelinated fibers. Along with the relatively small amounts of electrical energy needed to stimulate the myelinated fibers, it is noteworthy that such fibers exhibit a particular strength-duration curve in response to a specific width and amplitude of stimulation pulse.

The A and B fibers are stimulated with relatively narrow pulse widths, from 50 to 200 microseconds ($\mu s$), for example. A fibers exhibit slightly faster electrical conductivities than the B fibers, and slightly lower electrical stimulation thresholds. The C fibers are relatively much smaller, conduct electrical signals very slowly, and have high stimulation thresholds typically requiring wider pulse widths (e.g., 300–1000 $\mu s$) and higher amplitudes for activation. Although the A and B fibers may be selectively stimulated without also stimulating the C fibers, the magnitude and width of the pulse required for stimulating the C fibers would also activate A and B fibers.

Although electrical stimulation of the nerve fiber typically activates neural signals in both directions (bi-directionally), selective unidirectional stimulation is achievable through the use of special nerve electrodes and stimulating waveforms. As noted above, each axon of the vagus nerve normally conducts in only one direction.

In a paper on the effects of vagal stimulation on experimentally induced seizures in rats (*Epilepsia* (1990) 31 (Supp 2): S7–S19), Woodbury has noted that the vagus nerve is composed of somatic and visceral afferents (i.e., inward conducting nerve fibers which convey impulses toward a nerve center such as the brain or spinal cord) and efferents (i.e., outward conducting nerve fibers which convey impulses to an effector to stimulate it and produce activity). The vast majority of vagal nerve fibers are C fibers, and a majority are visceral afferents having cell bodies lying in masses or ganglia in the neck. The central projections terminate, by and large, in the nucleus of the solitary tract which sends fibers to various regions of the brain (e.g, the hypothalamus, thalamus, and amygdala); others continue to the medial reticular formation of the medulla, the cerebellum, the nucleus cuneatus and other regions.

Woodbury further notes that stimulation of vagal nerve afferent fibers in animals evokes detectable changes of the EEG in all of these regions, and that the nature and extent of these EEG changes depends on the stimulation parameters. Chase, in *Exp Neurol* (1966) 16:36–49, had also observed that vagal activation can affect the EEG activity of certain parts of the brain. The applicants herein postulate that synchronization of the EEG may be produced when high frequency (>70 Hz) weak stimuli activate only the myelinated (A and B) nerve fibers, and that desynchronization of the EEG occurs when intensity of the stimulus is increased to a level that activates the unmyelinated (C) nerve fibers. Woodbury also observes that vagal stimulation can produce widespread inhibitory effects on seizures and certain involuntary movements.

Extra-physiologic electrical stimulation of the vagus nerve has previously been proposed for treatment of epilepsy and various forms of involuntary movement disorders. Specifically, in U.S. Pat. No. 4,702,254 issued Oct. 27, 1987 to J. Zabara (referred to herein as "the '254 patent"), a method and implantable device are disclosed for alleviating or preventing epileptic seizures, characterized by abnormal neural discharge patterns of the brain. The '254 patent describes an implantable neurocybernetic prosthesis (NCP) which utilizes neurocybernetic spectral discrimination by tuning the external current of the NCP generator to the electrochemical properties of a specific group of inhibitory nerves that affect the reticular system of the brain. These nerves are embedded within a bundle of other nerves, and are selectively activated directly or indirectly by the tuning of the NCP to augment states of brain neural discharge to control convulsions or seizures. According to the patent, the spectral discrimination analysis dictates that certain electrical parameters of the NCP pulse generator be selected based on the electrochemical properties of the nerves desired to be activated. The patent further indicates that the optimum sites for application of the NCP generator output to produce the desired effects are the cranial nerves in general, and the vagus nerve in particular.

The NCP disclosed in the '254 patent may be activated either manually or automatically, to provide treatment for the duration of the seizure. Manual activation is performed when the patient experiences the aura at onset of the seizure. Alternatively, automatic activation may be triggered upon detection of instantaneous changes in certain state parameters immediately preceding or at onset of a seizure. Additionally, a prophylactic or preventive mode may be employed in which the NCP is activated periodically to reduce the occurrence and/or the intensity of the seizures. The NCP stimulator of the '254 patent is implanted in the patient's chest and is connected to electrodes installed at the selected point of signal application at the nerve site with the more negative electrode situated closer to the brain and the positive electrode further from the brain, along the vagus nerve.

There is substantial evidence to indicate that sleep is modulated by brain stem centers. Because these centers receive input from the vagus nerve, their activity can be affected by vagal stimulation. The following are some scientific papers of interest on this subject. In *Exp. Brain Res. Suppl.* (1984) 8:3–18, Sakai describes synchronized sleep (NREM) and desynchronized sleep (REM) and the brain centers which control them in the cat. Puizillout et al. showed, in *Brain Res.* (1976) 11:181–184, that vagal stimulation may increase the number or duration of REM episodes, the total amount of REM being found constant; and, in *Electroencephalog. Clin. Neurophysiol.* (1977) 42:552–563, that sleep cycles may be induced by stimulation of the vagus nerve. Another Puizillout et al. group reviewed, in *Exp. Brain Res. Suppl.* (1984) 8:20–38, literature on the evidence for involvement of the nucleus of the solitary tract and vagal afferents in modulation of sleep cycles. In *Brain Res. Bull.* (1985) 15:437–441, Juhasz et al. showed that vagal stimulation directly affects reticular and ventro-posterior-medial nuclei of the cat thalamus; neural activity recorded depended on stimulus parameters, sleep state and site of recording.

SUMMARY OF THE INVENTION

The present invention is directed to methods and devices for treating and controlling sleep disorders by selective stimulation of the vagus nerve (the tenth cranial nerve) in a predetermined manner to modulate its electrical activity, and thereby synchronize or desynchronize the patient's EEG and/or modify the patient's sleep patterns according to the specific nature of the sleep disorder under treatment. In general, the normal EEG of an awake subject exhibits low voltage and relatively fast activity. Normally also, the EEG activity slows down during sleep, and displays higher voltage. NREM sleep stage patterns and REM sleep patterns have been discussed briefly in the above background section of this document.

In the preferred methods of the invention, disorders associated with abnormally little sleep (insomnia) are treated by modulating the patient's vagal activity with electrical signal parameters which produce a high voltage synchronous EEG typically seen in the intermediate stages of sleep; whereas disorders associated with abnormally excessive sleep (in terms of suddenness, depth or duration) are treated by modulating the patient's vagal activity with electrical signal parameters or stimuli which desynchronize the patient's EEG activity. Both of these categories may employ a sensing (automatic) mode and/or a patient (manual) activation mode for delivery of the therapy.

The apparatus of the invention includes a neurostimulator (preferably but not necessarily implantable) to selectively apply the desired therapy to treat the sleep disorder of interest by modulating the electrical activity of the patient's vagus nerve in a predetermined manner. The neurostimulator is programmed by the attending physician to provide the desired therapeutic modality for that purpose.

Selection among various strategies for vagal modulation to treat the sleep disorder depends on a number of factors. These include (i) a consideration of which of the nerve fibers are to be subjected to stimulation; (ii) the modality for achieving synchronization or desynchronization of the EEG; (iii) whether some type of physiologic signal is generated which can be detected and employed to trigger the modulation; and/or (iv) whether a "carryover" or refractory period occurs after modulation in which the benefit of the modulation is maintained. Although these are not all of the factors to be considered for selecting a stimulation strategy for treatment of the disorder, nor necessarily listed in order of importance, they are indicative of considerations which may apply in a specific case.

In the treatment according to the invention, different signal parameters and threshold curves are used to activate the various fibers of the patient's vagus nerve for selective modulation of the electrical activity thereof. By appropriately setting pulse width and amplitude of the electrical signal to be delivered by the neurostimulator to the patient's vagus nerve, the nerve fibers can be selectively stimulated, such as A and not B and C; or A and B, but not C; or A, B and C. Various related factors, however, must be considered in the selection process. For example, because the C fibers conduct signals very slowly, they are not highly responsive to techniques of fast stimulation. Therefore, if it were desired to increase desynchronous activity of the EEG by stimulation of the C fibers at 50 Hz, for example, for treatment of narcolepsy in a particular patient, it would be prudent to use a short pulse train for the stimulus. This is because the fibers would become refractory to the stimulation within a relatively short time interval and thus incapable of tracking the pattern of a longer train. After a suitable recovery period, another short pulse train may be applied to achieve further treatment. The precise pattern to be used, the length of the time intervals on and off, will depend upon and be adjusted to the individual patient and the particular sleep disorder being treated.

Furthermore, proper designation of amplitude and frequency range of the applied signals allows tuning of the fibers for EEG synchronization or desynchronization, for control of the disorder. Desynchronization of the EEG has been found to be achieved by stimulation of the vagus nerve at frequencies in the range from 20 to 75 Hz at levels above 0.1 volt, but requires signals greater than 3 volts at frequencies above 75 Hz. If the frequency is above 75 Hz and the signal is below 3 volts, EEG synchronization is achieved. The actual voltage required depends on the type and geometry of the electrode and the impedance of the electrode-tissue interface.

According to the invention, the basic stimulation strategy is to modulate the electrical activity of the vagus nerve to synchronize or desynchronize the patient's EEG, and, in appropriate cases, to produce the desired patterns of REM and NREM sleep, depending on the particular sleep disorder and the individual patient. In part, this involves modulating the activity of a number of brain structures, including the limbic system, the hippocampus, and the reticular formation, the latter being of particular importance in the control of sleep. As described by Rutecki in *Epilepsia* (1990) 31 (Supp. 2): S1–S6, the vagus nerve projects directly or indirectly to these brain structures. The strategy may be implemented by use of a detection system specific to the sleep disorder of interest, including, if necessary, sense signal analysis circuitry, to trigger automatic stimulation of the vagus nerve. Alternatively or additionally, the neurostimulator may be adapted for manual activation by the patient upon recognizing onset or continuation of the disorder (such as inability to sleep, or an overwhelming desire to sleep). For example, for automatic delivery of the stimulus therapy to the narcoleptic patient, surface electrodes may be implanted in the head to measure EEG activity, and to activate the neurostimulator to deliver stimuli for desynchronizing the synchronous high voltage slow wave EEG activity and increasing the background desynchronous activity upon detection of sudden synchronous EEG activity. A more simple, but effective detection strategy for narcolepsy attacks is to implant a miniaturized motion detector to sense a sudden drop of the patient's head. For sleep apnea, the detection may be of the respiratory muscle (chest) movement or of air flow through the nostril(s), to trigger stimulation at onset of an apneic episode.

A stimulation strategy which does not require specific detection involves the use of circadian or other rhythmic programming to automatically activate vagal stimulation in a manner to induce sleep during the normal nighttime cycle for the insomniac patient, or to arouse and stimulate alertness during the normal daytime cycle for the hypersomniac patient. In general, however, a detection strategy appropriate to the disorder of interest is selected to initiate the proper stimulation strategy.

Broadly, then, the present invention is directed to apparatus and methods which employ a neurostimulator device, preferably implantable, for therapy or treatment of sleep disorders through nerve stimulation. The modulating signals applied to the vagus nerve may stimulate or inhibit neural signals to produce excitatory or inhibitory neurotransmitter release, but for purposes of this disclosure both situations are included within the term "stimulating". It should be emphasized that although the preferred nerve site for application of the modulating signals is the vagus nerve, effective treatment may be achieved through application of the stimulus to one or more other nerves, particularly among the cranial nerves, and such treatment is deemed to be within the ambit of the present invention.

Accordingly, it is another object of the present invention to apply the techniques of selective modulation of vagus nerve electrical activity, using a neurostimulator device which may be implantable, or disposed external to the body with only a small portion of the circuitry implanted or with only the nerve electrode (s) and associated lead (s) implanted percutaneously in the body, to the treatment or control of sleep disorders.

A more specific object of the invention is to provide methods and apparatus responsive to detected symptoms characteristic of or associated with certain sleep disorders for applying preprogrammed electrical stimuli to a cranial nerve and particularly the vagus nerve of the patient to modulate the electrical activity of afferent fibers of the nerve as part of a therapy designed to treat or control the specific disorder, such as by selectively synchronizing or desynchronizing the patient's EEG in the case of the insomniac or hypersomniac patient, respectively.

Another object of the invention is to provide methods of treating and controlling a sleep disorder by sensing a symptom of the disorder and automatically or manually responding thereto by modulating electrical activity of the appropriate brain or brain stem centers through the application of preselected stimuli to the patient's vagus nerve.

BRIEF DESCRIPTION OF THE DRAWINGS

The above and still further objects, aspects, features and attendant advantages of the present invention will be better understood from a consideration of the ensuing detailed description of a presently preferred embodiment and method thereof, taken in conjunction with the accompanying drawings, in which:

FIGS. 2A and 2B are each a simplified fragmentary illustration of a preferred embodiment of the stimulus generator and lead/electrode system of the neurostimulator implanted in the patient's body, and of respective sensor systems suitable for detecting certain sleep disorders;

FIG. 3 is a detailed fragmentary illustration of the nerve electrode as implanted on the vagal nerve in the neck of the patient for modulating vagal activity;

DESCRIPTION OF THE PRESENTLY PREFERRED EMBODIMENTS AND METHODS

Figure 1:
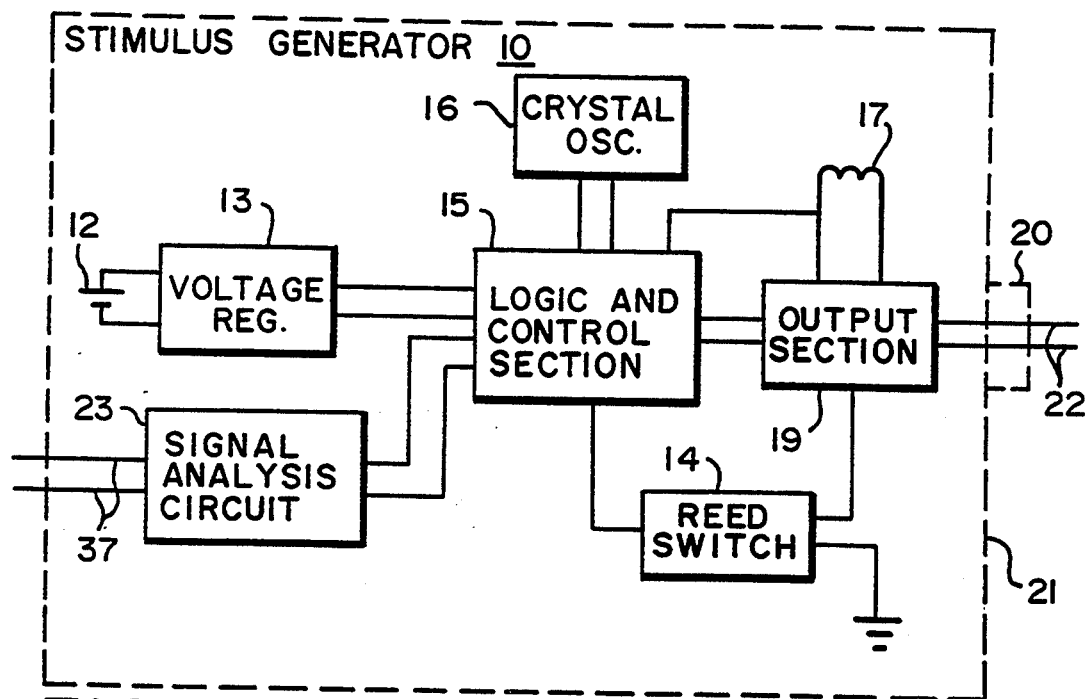
FIG. 1 is a simplified block diagram of an implantable neurostimulator electronics package (stimulus generator) for use (with appropriate parameter settings and ranges) in treating sleep disorders according to the present invention.

Referring now to the drawings, a block diagram of the basic components of the stimulus generator of a neurostimulator and their interrelationship is illustrated in FIG. 1, and further details of location of an implantable version of the device and the associated lead/electrode system are shown in FIGS. 2 and 3. A generally suitable form of neurostimulator for use in the apparatus of the present invention is disclosed in copending U.S. patent application Ser. No. 07/434,985, now U.S. Pat. No. 5,154,172, issued Oct. 13, 1992 to Terry, Jr. et al. (referred to herein as "the '172 patent") et al., assigned to the same assignee as the instant application. The specification of the '172 patent is incorporated herein in its entirety by reference, but certain portions of it are summarized in this application for the sake of convenience to the reader.

The neurostimulator utilizes a conventional microprocessor and other standard electrical and electronic components, and in the case of an implanted device, communicates with a programmer and/or monitor located external to the patient's body by asynchronous serial communication for controlling or indicating states of the device. Passwords, handshakes and parity checks are employed for data integrity. The neurostimulator also includes means for conserving energy, which is important in any battery operated device and especially so where the device is implanted for medical treatment of a disorder, and means for providing various safety functions such as preventing accidental reset of the device.

Figure 2B:
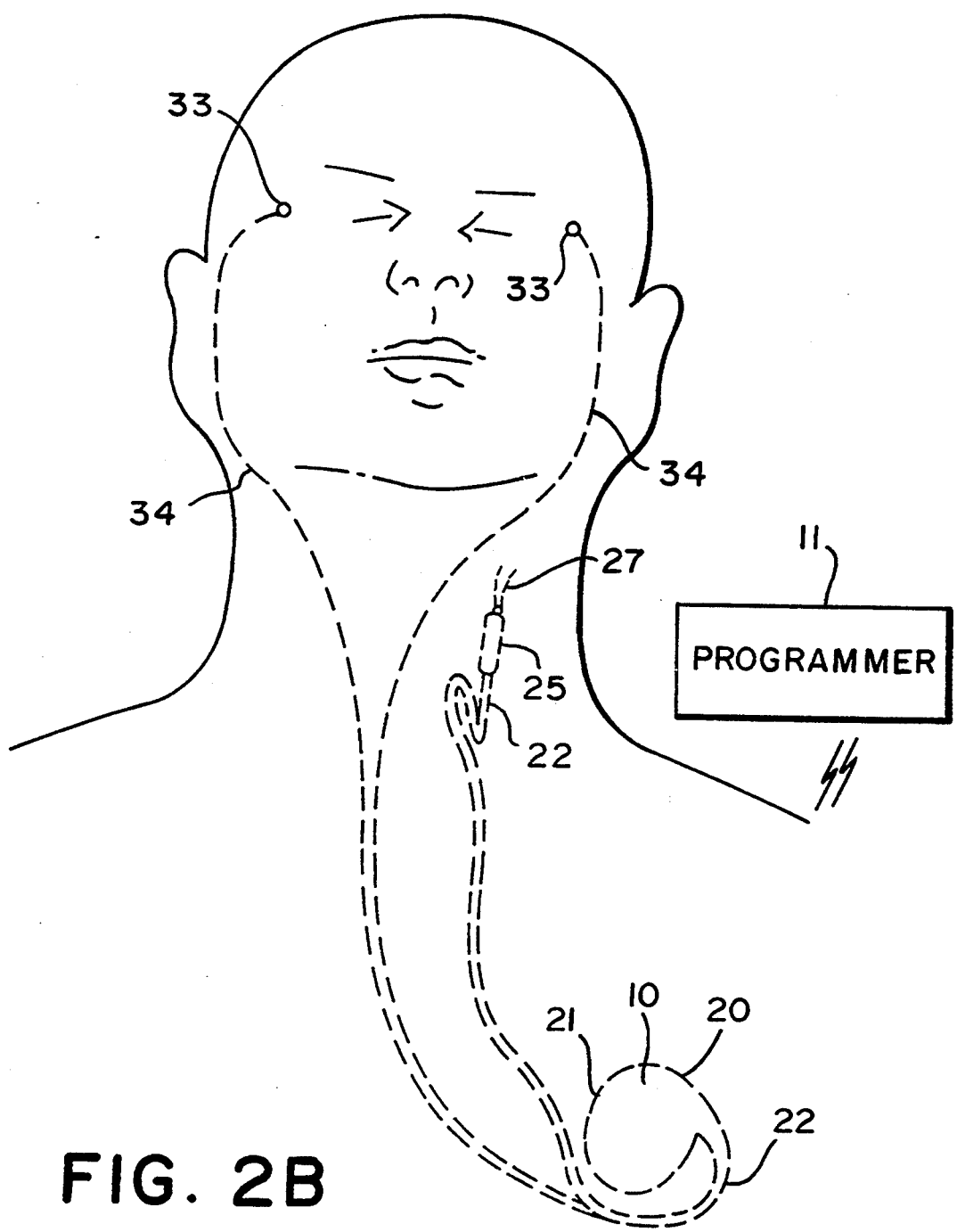

The stimulus generator 10 (FIG. 1) is preferably adapted to be implantable in the patient's body, in a pocket formed by the surgeon just below the skin in the chest as shown in FIG. 2A, although a primarily external neurostimulator may alternatively be employed. The neurostimulator also includes implantable stimulating electrodes (described below) together with a lead system 22 for applying the output signal of the stimulus generator to the patient's vagus nerve. Components external to the patient's body include a programming wand for telemetry of parameter changes to the stimulus generator and monitoring signals from the generator, and a computer and associated software for adjustment of parameters and control of communication between the generator, the programming wand and the computer. These external components of the system are shown for the sake of simplicity as programmer 11 in FIG. 2B.

In conjunction with its microprocessor-based logic and control circuitry, the stimulus generator 10 or other implanted or external circuitry includes detection circuitry for sensing an event indicative of onset or ongoing presence of the sleep disorder to trigger automatic delivery of the stimulating signal. For example, EEG surface or depth electrodes may be implanted to sense EEG characteristics associated with the particular disorder, eye movement sensors may be implanted to detect REM or NREM sleep, a respiration detector may be implanted in or worn externally by the sleep apnea patient to sense cessation of breathing, or an accelerometer may be implanted in the narcoleptic patient to respond to a sudden attack of deep sleep, in each case to trigger the appropriate vagal stimulation therapy programmed into the neurostimulator for the individual patient. Further details of the detection systems will be discussed presently herein. Use of certain sensors, such as depth EEG electrodes, may involve more delicate electrode/lead implantation procedures and the need for associated analyzing circuitry not required with others, but the use of such sensors can be the most suitable and accurate technique presently achievable for detecting the serious sleep disorder of interest and initiating appropriate therapy. The stimulus generator is designed, implemented and programmed to deliver a selectively patterned stimulating signal to modulate the electrical activity of the vagus nerve in a manner designed to treat and control the disorder.

As shown in FIG. 1, stimulus generator 10 includes a battery (or set of batteries) 12, which may be of any reliable long-lasting type conventionally employed for powering implantable medical electronic devices (such as batteries employed in implantable cardiac pacemakers or defibrillators). In the preferred embodiment of the stimulus generator, the battery is a single lithium thionyl chloride cell. The terminals of the cell 12 are connected to the input side of a voltage regulator 13. The regulator smoothes the battery output to produce a clean, steady output voltage, and provides enhancement thereof such as voltage multiplication or division if necessary for a specific application.

Regulator 13 supplies power to logic and control section 15, which includes a microprocessor and controls the programmable functions of the device. Among these programmable functions are output current or voltage, output signal frequency, output signal pulse width, output signal on-time, output signal off-time, daily treatment time for continuous or periodic modulation of vagal activity, and output signal-start delay time. Such programmability allows the output signal to be selectively crafted for application to the stimulating electrode set (FIGS. 2 and 3) to obtain the desired modulation of vagal activity for treatment and control of the specific sleep disorder. Timing signals for the logic and control functions of the generator are provided by a crystal oscillator 16. A magnetically-actuated reed switch 14 is incorporated in the electronics package to provide the generator with the capability for patient activation thereof (by use of an external magnet, not shown, placed immediately adjacent to the package or its implant site).

Built-in antenna 17 enables communication between the implanted stimulus generator and the external electronics (including both programming and monitoring devices) to permit the device to receive programming signals for parameter changes, and to transmit telemetry information, from and to the programming wand. Once the system is programmed, it operates continuously at the programmed settings until they are reprogrammed (by the attending physician) by means of the external computer and the programming wand.

Figure 5:
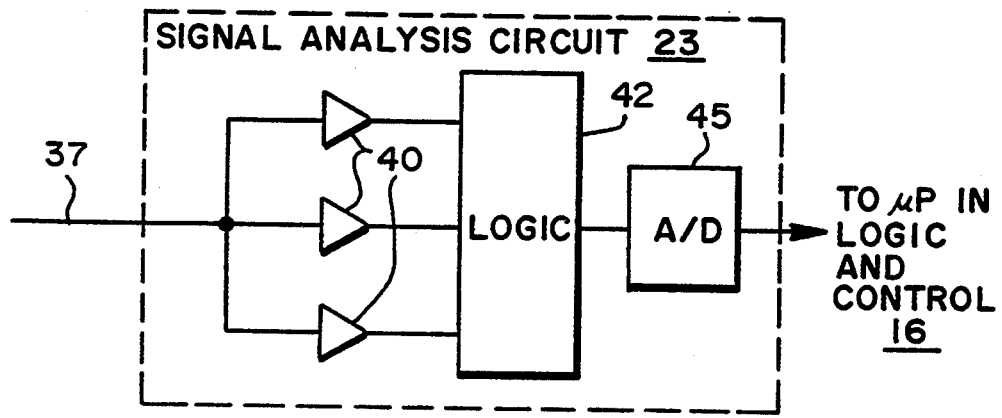
FIG. 5 is a simplified block diagram of an EEG spectral analysis circuit which may be used in the stimulus generator in conjunction with an EEG detection system useful for treating insomnia and hypersomnia.

Logic and control section 15 of the stimulus generator 10 controls an output circuit or section 19 which generates the programmed signal levels appropriate to the disorder being treated. The output section and its programmed output signal are coupled (directly, capacitively, or inductively) to an electrical connector 20 on the housing 21 of the generator and to lead assembly 22 connected to the stimulating electrodes (FIGS. 2 and 3). A sense signal analysis circuit 23 is provided within the generator housing 21, with connections to the microprocessor in logic and control section 15 and to the sensing electrodes. An exemplary sense signal analysis circuit for use with implanted EEG sensing electrodes to cause the microprocessor to trigger delivery of therapy by the output circuit of the generator on detection of a selected event, is shown in FIG. 5 and will be described presently. The parameters of the stimulating signal of the implanted device may be calibrated by telemetry (via the programming wand) according to the needs of the particular patient and the results then programmed into the microprocessor for delivery of the appropriate treatment upon activation of the stimulus generator.

Housing 21 in which stimulus generator 10 is encased is hermetically sealed and composed of a material such as titanium which is biologically compatible with the fluids and tissue of the patient's body. Further details of suitable structure and operation of the neurostimulator, beyond those by which the device is adapted to treat the disorder as described herein, are available in the '172 patent, to which the reader is referred.

FIG. 2A, for example, illustrates the preferred location of implanted generator 10, in case 21 with connector 20, in the patient's chest in a cavity formed by the implanting surgeon just below the skin, much as a pacemaker pulse generator would be implanted. A stimulating nerve electrode set 25 (FIG. 3) is conductively connected to the distal end of insulated electrically conductive lead assembly 22 which is attached at its proximal end to connector 20. Electrode set 25 is a bipolar stimulating electrode, preferably of the type described in U.S. Pat. No. 4,573,481 issued Mar. 4, 1986 to Bullara. The electrode assembly is surgically implanted on the vagus nerve 27 in the patient's neck. The two electrodes 25-1 and 25-2 are wrapped about the vagus nerve, and the assembly is secured to the nerve by a spiral anchoring tether 28 preferably as disclosed in U.S. Pat. No. 4,979,511 issued Dec. 25, 1990 to Reese S. Terry, Jr. and assigned to the same assignee as the instant application. Lead(s) 22 is secured, while retaining the ability to flex with movement of the chest and neck, by a suture connection 30 to nearby tissue.

The open helical design of electrode assembly 25 (described in detail in the above-cited Bullara patent), which is self-sizing and flexible, minimizes mechanical trauma to the nerve and allows body fluid interchange with the nerve. The electrode assembly conforms to the shape of the nerve, providing a low stimulation threshold by allowing a larger stimulation contact area. Structurally, the electrode assembly comprises two ribbons of platinum constituting the electrodes which are individually bonded to the inside surface of each of the first two spiral loops 25-1 and 25-2 of a three-loop helical assembly, and the two lead wires are respectively welded to the conductive ribbon electrodes. The remainder of each loop is composed of silicone rubber, and the third loop acts as the tether 28 for the electrode assembly. The inner diameter of the helical bipolar electrode assembly may typically be approximately two millimeters (mm), and an individual spiral is about seven mm long (measured along the axis of the nerve).

For purposes of detecting the EEG characteristics associated with insomnia or hypersomnia sleep disorder, depth EEG sense electrodes 36 (FIG. 2A) may be implanted in spaced apart relation through the skull, and connected to leads 37 implanted via a catheter or other suitable means (not shown) and extending along the scalp and temple and then along the jawline through the neck and chest tissue to the sense signal analysis circuit 23 of stimulus generator 10. Alternatively, or additionally, if prescribed by the attending physician, eye movement sensing electrodes 33 may be implanted at or near the outer periphery of each eye socket in a suitable location to sense muscle movement, or actual eye movement by placement about the nerves which control such movement, as shown in FIG. 2B. The sense electrodes 33 are utilized to detect REM and NREM sleep, and are electrically connected to leads 34 implanted and extending toward the ears and then generally along the same path and in the same manner as described above for the EEG sense electrode leads. In this case, the signal analysis circuit would be simplified, consisting for example of a logic circuit which generates an activation command to the microprocessor upon detecting a predetermined count within a set period of time, indicative of REM sleep.

Figure 6A:
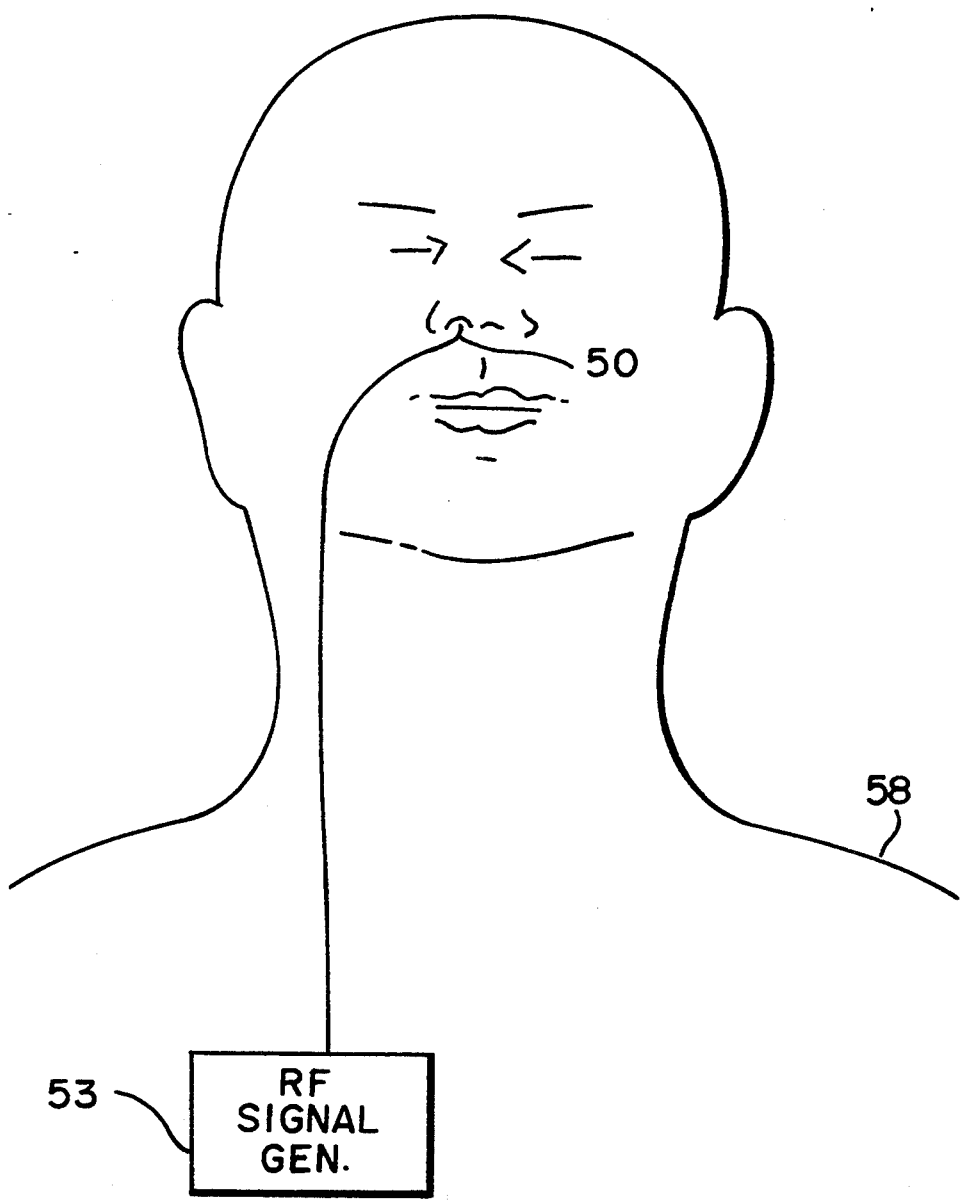
FIG. 6A is another simplified fragmentary illustration, similar to that of FIG. 2A, but here, of an exemplary sensor system suitable for detecting sleep apnea, two alternative embodiments of which are shown in FIGS. 6B and 6C, and, in FIG. 6D, a sensor system suitable for detecting narcolepsy attacks, which may be worn externally by or implanted in the patient.

For sleep apnea patients, the cessation of respiration is detected, in a preferred embodiment, by an externally-positioned breathing sensor placed in the patient's nostril as shown at 50 in FIG. 6A. A suitable breathing sensor merely detects the presence or absence of nasal air flow and is worn in or near one nostril, only at night or anytime that the patient retires to sleep, such as at nap times for infant or elderly patients. Processing of the nasal air flow signal is performed by a suitable external circuit 53 which is adapted to generate an activation command to the microprocessor of logic and control circuit 15. A suitable processing circuit is an external RF signal generator positioned in the vicinity of the implanted stimulus generator 10 and triggered by a sustained absence of nasal air flow for a predetermined interval of time. The selected time interval should be sufficiently long to reasonably assure that the patient has stopped breathing momentarily, and yet sufficiently short to allow the detection to be made and the vagal stimulation to be commenced before the patient's sleep is interrupted.

Although external devices are less attractive than implants to most patients, in this instance the cosmetic considerations are less significant because the external devices are worn or used by the sleep apnea patient only at times when the intention or expectation is to sleep. However, a totally implanted respiration detection system may be employed, if desired, for example using a device which senses movement of the patient's diaphragm associated with normal breathing. Preferably, the diaphragm movement is sensed by an impedance detector 59 (FIG. 6B), or alternatively, by plural electrodes for detecting physical movement of the muscle (shown as diaphragm movement detector 60 in FIG. 6C), implanted in the chest somewhere below the shoulder 58 of the patient. The detector generates a signal indicative of absence of diaphragm movement for a time interval set according to the abovementioned criteria, which is conveyed by implanted lead 61 or 62 to trigger application of vagal stimulation by generator 10 under the command of the microprocessor.

Figure 6D:
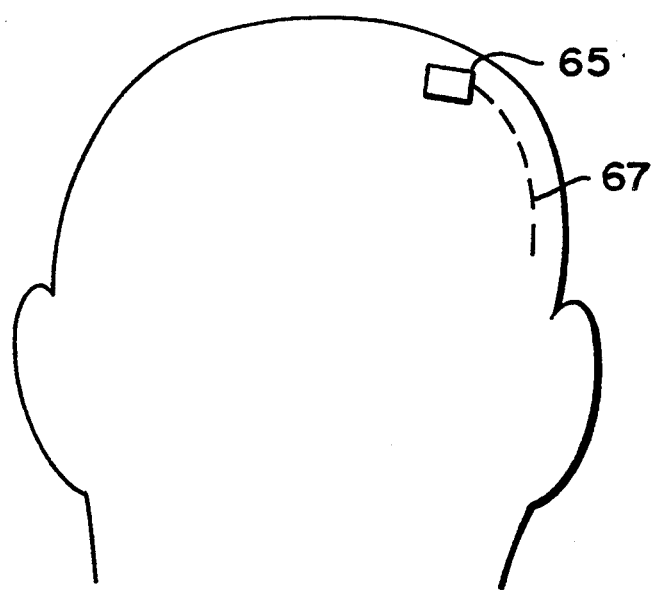
Figure 6B:
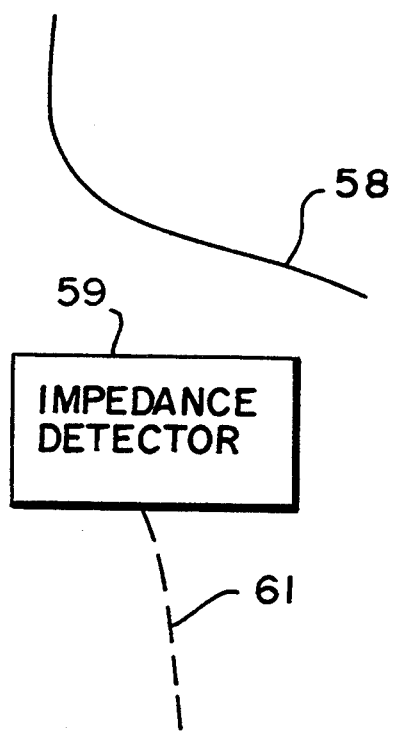
Figure 6C:
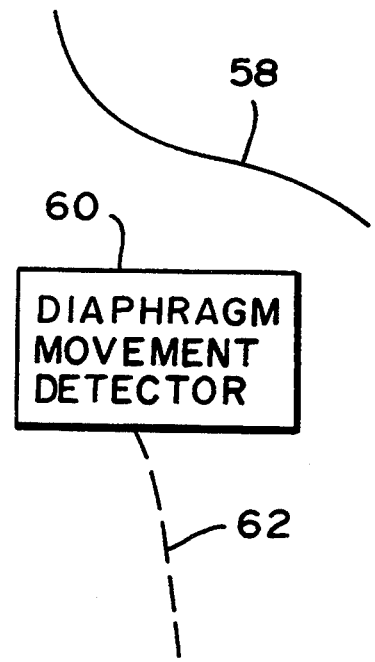

For the narcoleptic patient, a miniaturized accelerometer in the form of a movement detecting electronic or electromechanical switch, for example, may be implanted beneath the skin as generally shown at 65 in FIG. 6D. The accelerometer position is selected to respond to sudden nodding or dropping of the patient's head, which results from the brief attack of deep sleep characteristic of narcolepsy, to generate a signal on implanted lead 67 to trigger stimulation of the vagus nerve.

The stimulus generator may be programmed with an IBM-compatible personal computer (not shown) using programming software of the type copyrighted by the assignee of the instant application with the Register of Copyrights, Library of Congress, or other suitable software based on the description herein, and a programming wand (not shown). The wand and software permit noninvasive communication with the generator after the latter is implanted. The wand is preferably powered by internal batteries, and provided with a "power on" light to indicate sufficient power for communication. Another indicator light is preferably provided to show that data transmission is occurring between the wand and the generator.

Figure 4:
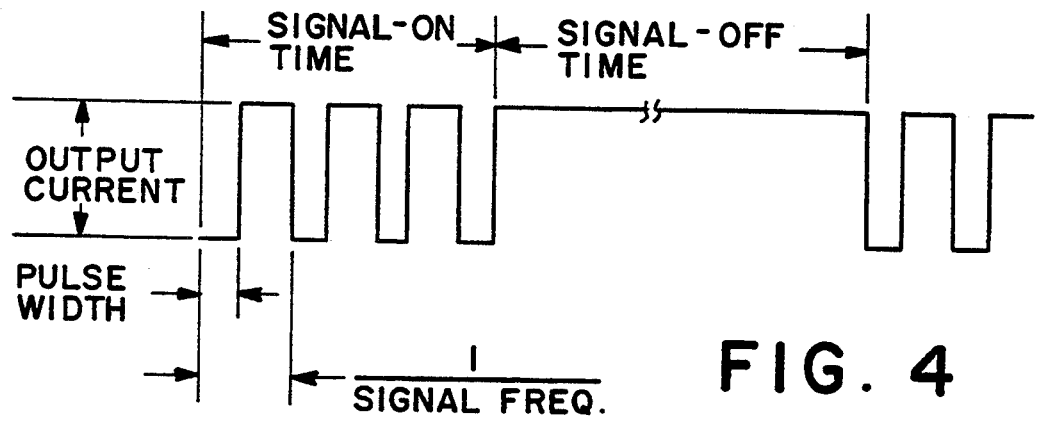
FIG. 4 is an illustrative idealized electrical output signal waveform of the stimulus generator useful for clarifying relevant parameters of the signal developed by the stimulus generator for application to the nerve.

The operation of stimulus generator 10 to control and treat sleep disorders will be described with reference to FIG. 4, which illustrates the general nature, in idealized representation, of the output signal waveform delivered by output section 19 of the neurostimulator to electrode assembly 25. This illustration is presented principally for the sake of clarifying terminology, including the parameters of output signal on-time, output signal off-time, output signal frequency, output signal pulse width, and output signal current or voltage.

In the treatment of sleep disorders according to the invention, the stimulation strategy is to program the neurostimulator to synchronize the patient's EEG activity in the case of insomniac patients, and to desynchronize the EEG activity in the case of hypersomniac, narcoleptic or sleep apnea patients. For synchronization, the parameters of the stimulus signal may be programmed, for example, at a frequency of 90 Hz, an output current of 1.0 mA, and a pulse width of 0.10 ms for the pulse waveform. For desynchronization, the corresponding parameters of an exemplary pulse waveform would be 20 Hz, 1.5 mA, and 0.5 ms. A patient suffering from insomnia may simply activate the neurostimulator when he or she is unable to sleep. This may be accomplished in a number of different ways, one example being to place an external magnet directly over the site of the implanted stimulus generator to actuate the reed switch 14 (FIG. 1).

A suitable range of stimulation parameters for synchronization or desynchronization of the patient's EEG activity, as appropriate, and the typical value of each parameter of the stimulating output signal for treatment of the disorder are as follows:

|  | Range | Desynch, Typical | Synch, Typical |
| --- | --- | --- | --- |
| Pulse Width | 0.05–1.5 ms | 0.5 ms | 0.1 ms |
| Output Current | 0.1–5.0 mA | 1.5 mA | 1.0 mA |
| Frequency | 5–150 Hz | 20 Hz | 90 Hz |
| ON Time | 5–5000 sec | 300 sec | 30 sec |
| OFF Time | 5–5000 sec | 20 sec | 30 sec |
| Frequency sweep | 10–100 Hz | Optional | |
| Random frequency | 10–100 Hz | Optional | |

As noted earlier herein, a technique for initiating stimulation without a specific detection system requires that the neurostimulator be programmed according to the circadian rhythm of the particular patient and the disorder being treated, to either desynchronize or synchronize the patient's EEG activity as appropriate.

A signal analysis circuit 23 for stimulus generator 10 (FIG. 1), suitable for processing the EEG waveform developed by surface or depth EEG electrodes, is shown in greater detail in FIG. 5. In this exemplary embodiment, the sensing electrodes are EEG electrodes such as 36 and associated leads 37 of FIG. 2, and the analysis circuit 23 is implemented for EEG detection and analysis. To that end, circuit 23 includes a plurality of parallel active sense signal bandpass filters 40 staged to provide selective filtering in the ranges from 0–2 Hz, 2–4 Hz and 15–20 Hz, for example; a logic circuit 42 to select the output of one filter from among the plurality of filters 40; and an analog/digital (A/D) converter 45. The outputs of the filters are individually sampled by the logic circuit 42, and the sampling rate, averaging time interval, and weighting assigned to each sense signal band are controlled by the microprocessor in the logic and control section 15 of the stimulus generator 10 (FIG. 1), to detect the EEG pattern. When the selected event is detected, the processed digital signal is supplied to the microprocessor to trigger application of the stimulating signal to the patient's vagus nerve.

As specified above, other types of signal processing circuits may be used depending on the specific type of detection required, or, in some instances, the output of the sensing device itself may be used directly without further processing.

Various features may be incorporated into the neurostimulator for purposes of the safety and comfort of the patient. For example, comfort would be enhanced by programming the output stimulus to ramp up during the first two seconds of stimulation, rather than to be delivered abruptly. Also, the implanted generator may be provided with a clamping circuit to limit the maximum voltage, to 14 volts for example, which is delivered to the vagus nerve. Such a maximum limit is designed to prevent injury to the patient's vagus nerve.

The programmable functions and capabilities of the neurostimulator are designed and implemented to permit noninvasive communication with the stimulus generator after it is implanted, which is useful for both activation and monitoring functions. Beyond the essential functions of the device, the programming software may readily be structured to provide straightforward menu-driven operation, HELP functions, prompts, and messages to facilitate simple and rapid programming while keeping the user fully informed of everything occurring at each step of a sequence. Programming capabilities should include capability to modify the adjustable parameters of the stimulus generator and its output signal, to test device diagnostics, and to store and retrieve telemetered data. It is desirable that when the implanted unit is interrogated, the present state of the adjustable parameters is displayed on the monitor of external PC so that the programmer may then conveniently change any or all of those parameters at the same time; and, if a particular parameter is selected for change, all permissible values for that parameter are displayed so that the programmer may select an appropriate desired value for entry into the neurostimulator.

Diagnostics testing should be implemented to verify proper operation of the device, and to indicate the existence of problems such as with communication, the battery, or the lead/electrode impedance. A low battery reading, for example, would be indicative of imminent end of life of the battery and need for implantation of a new device. The nerve electrodes are capable of indefinite use absent indication of a problem with them observed on the diagnostics testing.

Although a preferred embodiment and methods of treating and controlling sleep disorders according to the invention have been described herein, it will be apparent to those skilled in the field from a consideration of the foregoing description that variations and modifications of such embodiments, methods and techniques may be made without departing from the true spirit and scope of the invention. For example, although a totally implantable neurostimulator device is preferred (with the possible exception of the detection system), the electronic energization package may, if desired, be primarily external to the body. Stimulation can be achieved with an RF power device implemented to provide the necessary energy level. The implanted components may be limited to the lead/electrode assembly, a coil and a DC rectifier. Pulses programmed with the desired parameters would be transmitted through the skin with an RF carrier, and the signal thereafter rectified to regenerate a pulsed signal for application as the stimulus to the vagus nerve to modulate vagal activity. This would virtually eliminate the need for battery changes. The disadvantages of such an implementation are that the external transmitter must be carried by the patient, greater power is required for activation, and the output current to the nerve is less stable.

An external stimulus generator may be employed with leads extending percutaneously to the implanted nerve electrode set. The major problem encountered with this technique is the potential for infection, but it is useful to allow short term testing of the patient to determine whether the sleep disorder suffered by the patient under observation is amenable to successful treatment. If it is, a more permanent implant may be provided.

Accordingly, it is intended that the invention shall be limited only to the extent required by the appended claims and the rules and principles of applicable law.

What is claimed is:

1. A method of treating patients experiencing sleep disorders, which includes the steps of:

detecting a physiological event associated with the sleep disorder in the patient to be treated, and upon detection of such physiological event, applying a predetermined electrical stimulus to the patient's vagus nerve for modulating the electrical activity of the vagus nerve to alleviate the sleep disorder under treatment.

2. The method of claim 1, further including:

providing as the electrical stimulus a signal having programmable electrical parameters, and programming the electrical parameters of the signal to modulate the electrical activity of the vagus nerve to control the EEG activity of the patient.

3. The method of claim 2, wherein: and including:

programming at least some of the electrical parameters of the pulse waveform to synchronize or desynchronize the patient's EEG activity according to the nature of the sleep disorder under treatment.

4. The method of claim 3, wherein the detected event is one of (i) a desynchronous EEG pattern indicative of inability of the patient to sleep during nighttime hours, and (ii) a synchronous EEG pattern indicative of overwhelming desire of the patient to sleep during daytime hours; and the pulse waveform is programmed to synchronize the patient's EEG activity upon detected event (i), and to desynchronize the patient's EEG activity upon detected event (ii).

5. The method of claim 3, wherein:

the disorder under treatment is sleep apnea, and including:

detecting the physiological event by sensing a predetermined sustained period without respiration by the patient, and programming the pulse waveform electrical parameters to modulate the electrical activity of the vagus nerve, upon application of the pulse waveform to the vagus nerve, to desynchronize the patient's EEG upon sensing said predetermined sustained period without respiration.

6. The method of claim 3, including:

programming the electrical parameters of the pulse waveform including pulse width, output current or voltage, frequency, on time and off time.

7. The method of claim 3, wherein:

the disorder under treatment is insomnia, and including:

detecting the physiological event by sensing a respiration pattern of the patient indicative of wakefulness during normal nocturnal hours, and programming the pulse waveform electrical parameters to modulate the electrical activity of the vagus nerve, upon application of the pulse waveform, to the vagus nerve, to synchronize the activity of the patient's EEG upon sensing said respiration pattern indicative of wakefulness.

8. The method of claim 3, wherein the disorder under treatment is hypersomnia, and the pulse waveform signal parameters are programmed to desynchronize the activity of the patient's EEG.

9. The method of claim 1, wherein the detected event includes one of (i) an EEG pattern of the patient reflecting presence of the sleep disorder under treatment, (ii) a sudden uncontrolled nodding of the patient's head, and (iii) a cessation of respiration by the patient.

10. The method of claim 9, wherein
the predetermined signal has electrical parameters programmed to stimulate the vagus nerve to cause desynchronization of the patient's EEG upon detected event (ii).

11. The method of claim 1, wherein
the event is detectable by the patient, and the electrical signal is manually activatable.

12. The method of claim 1, wherein
the step of detecting the event is performed by sensing abdominal impedance changes associated with respiration by the patient indicative of the sleep disorder under treatment, to signal the need for applying the predetermined electrical stimulus to the patient's vagus nerve.

13. The method of claim 12, wherein
the step of sensing is performed to detect an abnormally along time interval in which the patient has stopped breathing.

14. The method of claim 12, wherein
the step of sensing is performed to detect respiration typically associated with a state of sleeplessness of the patient, during normal nocturnal hours.

15. A method of treating patients with sleep disorder, which includes
generating an electrical signal having a predetermined set of parameters,
programming the electrical signal by adjusting said parameters to predetermined values according to the sleep disorder under treatment,
detecting the presence of the sleep disorder under treatment, and, in response to such detection,
applying the programmed electrical signal to a selected cranial nerve of the patient to modulate the electrical activity of the selected cranial nerve to alleviate the sleep disorder under treatment.

16. The method of claim 15, wherein
said electrical signal is a pulse waveform, and including:
selecting the patient's vagus nerve as the cranial nerve to which the signal is to be applied, and
applying the programmed pulse waveform to a nerve electrode implanted on the patient's vagus nerve.

17. The method of claim 16, including
programming the parameter values of the pulse waveform including pulse width, output current, frequency, on time and off time.

18. In a method of treating patients with sleep disorders, the step of applying an electrical signal with parameters programmed to alleviate the sleep disorder under treatment to the vagus nerve of the patient to modulate the electrical activity thereof at predetermined times and for predetermined time intervals during the patient's circadian cycle.

19. A device for treating sleep disorders in human patients, comprising:
stimulus means responsive to being energized for generating an electrical waveform having adjustable parameter values,
electrode means structurally adapted to be implanted on a patient's cranial nerve which, when the electrical activity of the nerve is modulated by an applied electrical signal, evokes a predictable response in the EEG activity of the patient according to the parameter values of the applied electrical signal, the electrode means further structurally adapted to be electrically connectable to the stimulus means for delivering the electrical waveform generated by the stimulus means to said cranial nerve of the patient to modulate its electrical activity,
programming means operatively associated with said stimulus means for controllably adjusting the parameter values of the electrical waveform generated by said stimulus means, and
control means responsive to the occurrence of an event associated with the sleep disorder to be treated for energizing the stimulus means to generate said electrical waveform for application to the electrode means when connected to the stimulus means, so that the adjusted parameter values of the electrical waveform are delivered to said cranial nerve on which the electrode means are implanted and modulate its electrical activity to controllably vary the patient's EEG activity and alleviate the sleep disorder under treatment.

20. The invention of claim 19, wherein:
said programming means includes means for limiting adjustment of the parameter values of the waveform to a range of values predetermined to be suitable for modulating the electrical activity of the vagus nerve to synchronize or desynchronize the activity of the patient's EEG according to whether the sleep disorder under treatment is insomnia-related or hypersomnia-related, respectively.

21. The invention of claim 19, wherein:
said event is a physiological response of the patient indicative of the manifestation of the sleep disorder under treatment, and
said control means includes sensing means for detecting said physiological response to initiate the application of said waveform to said electrode means.

22. The invention of claim 21, wherein
said sensing means includes means for detecting the EEG activity of the patient.

23. The invention of claim 21, wherein
said sensing means includes means for detecting a sustained abnormal period of cessation of respiration of the patient.

24. The invention of claim 23, wherein
said means for detecting cessation of respiration includes means responsive to the absence of movement of the patient's diaphragm for sensing said sustained abnormal period of cessation of respiration.

25. The invention of claim 23, wherein
said means for detecting cessation of respiration includes means responsive to the absence of nasal air flow by the patient.

26. The invention of claim 21, wherein
said sensing means includes means for detecting a sudden uncontrolled nodding of the patient's head.

27. The invention of claim 21, wherein
said sensing means includes
an abdominal impedance detector, and
means responsive to predetermined changes in detected abdominal impedance to initiate the application of said waveform to said electrode means.

28. The invention of claim 19, wherein:
said event is a designated time during the circadian cycle of the patient when the patient should be sleeping, and
said control means includes timing means to energize said stimulus means and thereby cause the application of said waveform to said electrode means at said designated time for a predetermined time interval.

29. A method for use in advancing the treatment and control in patients of sleep disorders detectable by an implanted or external sensor, which comprises:
fabricating electrode means including an electrical lead with a stimulating electrode assembly at its distal end for implantation on a preselected cranial nerve of a patient which is responsive to electrical stimulation to selectively synchronize or desynchronize the patient's EEG,
implementing programmable stimulus generator means for generating, in response to detection by said sensor of the sleep disorder under treatment, electrical pulse sequences with selectively variable electrical parameters for selective application to the electrode means when implanted on said preselected cranial nerve,
incorporating electrical connector means in the stimulus generator means for electrically connecting the proximal end of the electrical lead to the stimulus generator means to receive the electrical pulse sequences generated by the stimulus generator means,
restricting the programmable ranges of values of the electrical pulse sequences to values which in combination will stimulate the small afferent fibers of the preselected cranial nerve when one or more programmed pulse sequences are applied to the nerve via the electrode means, for the purpose of selectively synchronizing or desynchronizing the patient's EEG activity according to the nature of the sleep disorder to be treated upon said detection of the disorder,
adapting the stimulus generator means for physician control of the programming, and
implanting the stimulus generator means and the electrode means into a patient suffering from a sleep disorder, for use in the treatment and control of the sleep disorder.

30. The method of claim 29, wherein the step of implementing the stimulus generator means includes arranging the stimulus generator means for selective variation of electrical parameters of the pulse sequences including pulse width, amplitude and frequency, sequence duration and intervals.

31. A method of treating patients suffering from a sleep disorder, which includes the steps of:
providing an electrical stimulus generator with an electrical output signal having parameters which are programmable within respective ranges predetermined, when the programmed output signal is properly applied to the vagus nerve of the patient, to relive a sleep disorder of a patient under treatment, and adapting the stimulus generator to generate its output signal upon selective activation of the stimulus generator,
implanting the stimulus generator in the patient's body, and implanting a nerve electrode to receive the output signal of the stimulus generator on the vagus nerve of the patient, and
programming at least some of the programmable parameters of the output signal of the stimulus generator according to the nature of the sleep disorder suffered by the particular patient under treatment to modulate the electrical activity of the vagus nerve, upon activation of the stimulus generator and consequent application of the programmed output signal thereof to the vagus nerve through the nerve electrode implanted thereon, to alleviate the sleep disorder suffered by the patient.

32. The method of claim 31, wherein:
the output signal of the stimulus generator is a pulse waveform and the programmable parameters thereof include pulse width, output current or output voltage, frequency, on time and off time, and
the implanting of the nerve electrode is performed by securing the electrode to the vagus nerve at a site in the patient's neck and electrically connecting the electrode via a conductive lead to the stimulus generator.

33. The method of claim 31, wherein:
the adapting of the stimulus generator to generate its output signal upon selective activation is performed by providing the stimulus generator with a sensor to detect an event associated with the sleep disorder under treatment and to activate the stimulus generator upon such detection, and including
implanting the sensor along with the stimulus generator.

34. Apparatus for therapeutically treating patients suffering from a sleep disorder such as insomnia or hypersomnia, in which the apparatus includes an implantable programmable neurostimulator device adapted to generate a programmed electrical output signal upon activation of the device, and an implantable electrical lead assembly connectable at its proximal end to the neurostimulator device to receive the programmed output signal thereof and having an electrode at its distal end adapted to be secured to a selected cranial nerve of the patient being treated, for electrical excitation of the selected cranial nerve to controllably modulate its electrical activity, characterized in that the apparatus further includes:
sensor means electrically coupled to the neurostimulator device for detecting the occurrence of a predetermined event associated with the sleep disorder of interest, and
activator means responsive to detection of such occurrence for activating the neurostimulator device to apply its programmed electrical output signal to the electrical lead assembly, and in which
the neurostimulator device includes means for rendering the output signal parameters thereof programmable only within respective ranges preselected to modulate the electrical activity of the selected cranial nerve so as to synchronize or desynchronize the patient's EEG according to whether the patient being treated is suffering from insomnia or hypersomnia, respectively.

35. The apparatus of claim 34, in which:
the neurostimulator device further includes manual activation means for alternative patient activation of the neurostimulator device to cause generation of the programmed electrical output signal thereof.

36. The apparatus of claim 34, in which the neurostimulator device includes:
means for generating the electrical output signal of the device in the form of a pulse waveform, and
selection means for programming signal parameters of the pulse waveform, including width of pulses, output current, output voltage, pulse frequency, and on time and off time of the waveform.

* * * * *